United States Patent
Ladisch (12)

(10) Patent No.: US 6,326,361 B1
(45) Date of Patent: Dec. 4, 2001

(54) GANGLIOSIDES WITH IMMUNOSUPPRESSIVE ACTIVITY

(75) Inventor: Stephan Ladisch, Pacific Palisades, CA (US)

(73) Assignee: The Regents of the University of California, Los Angeles, CA (US)

(*) Notice: Subject to any disclaimer, the term of this patent is extended or adjusted under 35 U.S.C. 154(b) by 0 days.

(21) Appl. No.: 08/071,304

(22) Filed: Jun. 2, 1993

Related U.S. Application Data

(63) Continuation of application No. 07/951,891, filed on Sep. 28, 1992, now abandoned, which is a continuation of application No. 07/677,437, filed on Mar. 29, 1991, now abandoned.

(51) Int. Cl.$^7$ .................. A61K 31/715; A61K 9/127; C07H 15/00
(52) U.S. Cl. .................. 514/54; 424/450; 536/4.1; 536/17.2
(58) Field of Search .................. 514/54; 424/450; 536/4.1, 17.2

(56) References Cited

U.S. PATENT DOCUMENTS

| | | | |
|---|---|---|---|
| 4,327,710 | * 5/1982 | De Loach et al. | 128/1 R |
| 4,730,058 | * 3/1988 | Ogawa et al. | 549/214 |
| 4,914,085 | * 4/1990 | Ochi | 514/25 |
| 5,173,219 | * 12/1992 | Kim | 264/4.6 |
| 5,229,376 | * 7/1993 | Alving et al. | 514/76 |

OTHER PUBLICATIONS

Agarwal et al; J. Immunol. 107(5):1448–1456 (1971).*
Miceli et al; ACTA Psychiat. Scand. 55:102–110 (1977).*
Yates et al; Chemical Abstracts 93: 112178r (1980).*
Whisler et al; J. Immunol. 125(5): 2106–2111 (1980).*
Hakomori; Ann. Rev. Biochem. 50: 733–764 (1981).*
Ladisch et al; Cancer RES. 43: 3808–3813 (1983).*
Ladisch et al; J. Clin. Invest. 74:2074–2081 (1984).*
Sugimoto et al; Garb. Res. 156: cl–c5 (1986).*
Yates et al; ACS Symp. Series 128(Cell Surface Glycolipids) pp 419–433 (1980).*
Hakomori et al; Adv. Exp. Med. Biol. 125: 247–261 (1980).*
Nagai et al; $1^{st}$ Intnat'l Symp. Hertie Found., Frankfurt "Search of the Case of MS and Other Chronic Diseases of the CNS" pp 127–138 (1980) Vorlag–Chemie.*
Jackson et al; Cellular Immunology 104:169–181 (1987).*
Cavaillon et al; Eur. J. Immunol. 16:1009–1012 (1986).*
Ladisch et al; J. Clin. Invest. 79:1879–1882 (Jun. 1987).*
Prokazova et al, Eur. J. Biochem. 172:1–6 (1988).*
Floutsis et al; Int. J. Cancer 43:6–9 (1989).*
Hachida et al; Transplant. Proc. 22(4):1663–1665 (Aug. 1990).*
Dillman et al; Molecular Biotherapy 4:117–121 (Sep. 1992).*

* cited by examiner

Primary Examiner—Kathleen Kahler Fonda

(57) ABSTRACT

A method for suppressing immune responses in animals by administering gangliosides to the animal. Gangliosides having terminal sialic acid groups are disclosed as being especially effective as immunosuppressive agents. The especially effective immunosuppressive gangliosides include $G_{M4}$ and $G_{M5}$. Ganglioside compositions for use in suppressing immune responses are also disclosed.

7 Claims, 1 Drawing Sheet

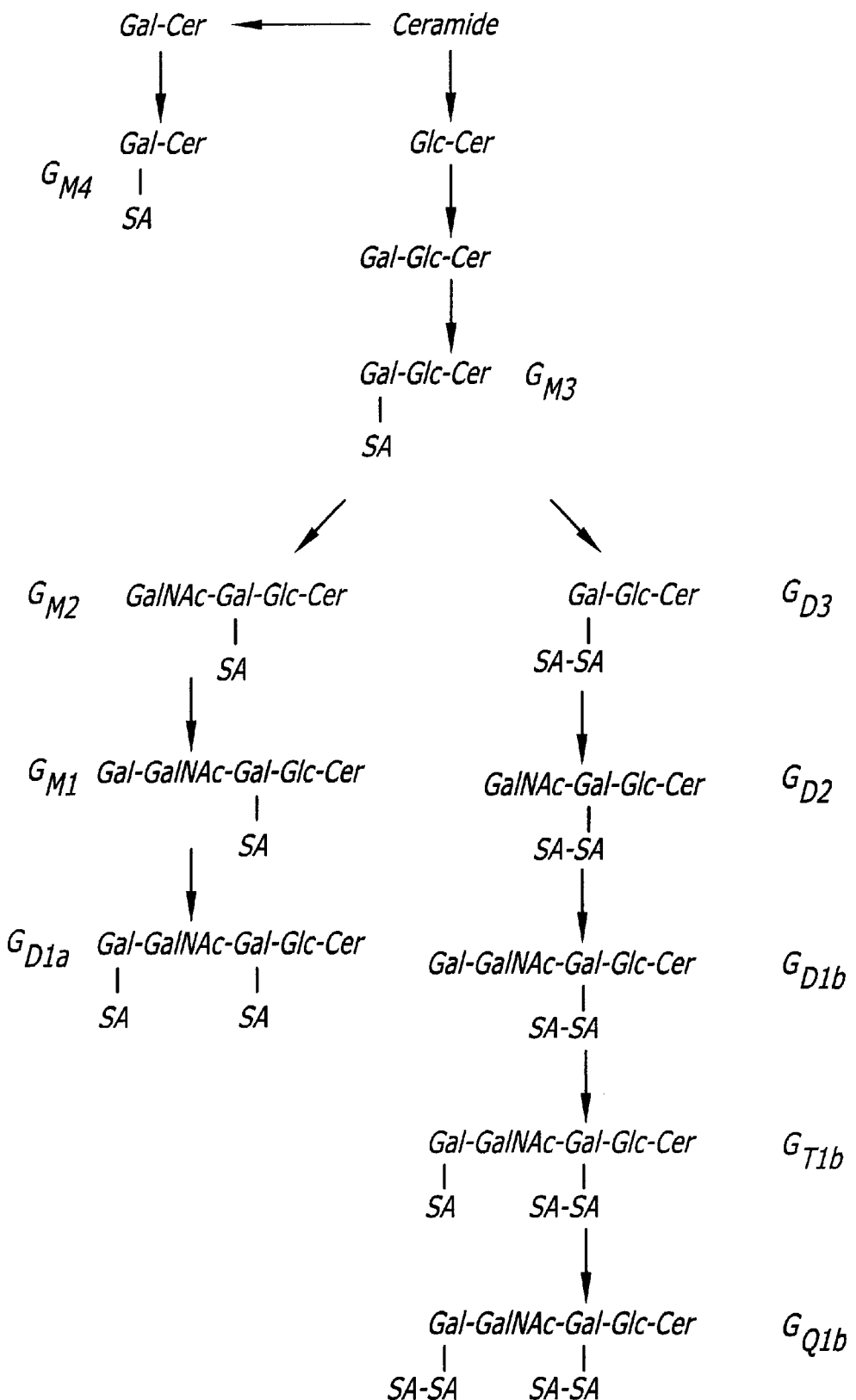

GANGLIOSIDES WITH IMMUNOSUPPRESSIVE ACTIVITY

This is a continuation of Ser. No. 07/951,891 filed on Sep. 28, 1992, now abandoned, which is a continuation of Ser. No. 07/677,437 filed on Mar. 29, 1991, also abandoned.

BACKGROUND OF THE INVENTION

1. Field of the Invention

The present invention relates to gangliosides and their use as immunosuppressive agents. More particularly, the present invention relates to the discovery that certain types of gangliosides demonstrate unexpectedly high immunosuppressive activity.

2. Description of the Background Art

Although the immune response is often seen as beneficial, in certain circumstances the immune response to an antigen can actually be harmful to the animal in which the immune response occurs. An example where the immune response creates a condition wherein the host is subject to serious pathologic sequelae is in such autoimmune diseases as lupus erythematosus, rheumatoid arthritis, diabetes, and Crohn's disease. In autoimmune diseases, the immune response is directed against host tissues, and therefore use of immunosuppressive agents is a treatment approach.

Another, and one of the most important, areas which often requires substantial immunosuppression is tissue transplantation, where the suppression of the immune response is crucial in order to prevent graft rejection by the host (host versus graft reaction, HVG) and graft rejection of the host (graft versus host rejection, GVH). Typically, the tissue which is grafted is allogeneic, where the inhibition of alloreactive T lymphocytes by immunosuppressive agents is essential to the prevention of allograft rejection. Depending upon the nature of the allograft (i.e. liver, kidney, or bone marrow), the course of immunosuppressive therapy may be relatively brief (months) or may have to be continued indefinitely (years to lifetime). All of the immunosuppressive agents used thus far have significant drawbacks relating either to direct toxicity on other organ systems or to failure to provide "balanced" immunosuppression. The latter problem has two distinct aspects; on one hand inadequate suppression of the immune response can lead to rejection, while on the other hand excessive immunosuppression can allow the development of opportunistic infections and neoplasia. Thus, the need to develop an effective non-toxic immunosuppressive agent which does not cause the above severe complications continues.

At present, multi-drug therapy, including cytotoxic agents, is utilized following organ transplantation. This typically comprises combination therapy, such as with cyclosporin A, azathioprine, and prednisone, the rationale being that each drug acts at a different stage in the immune response and that combination therapy will require lower doses of each individual drug, thus diminishing their dose-related side effects. However, the side effects remain significant while the efficacy of this form of therapy is still not satisfactory. Rejection continues to account for nearly 50% of graft losses in renal transplantation. And, distinguishing rejection from cyclosporin A nephrotoxicity may be difficult.

Another major cause of graft loss is systemic infection, usually by opportunistic infections, which require the tapering or cessation of immunosuppression, which leads to graft loss. Also, with such combination therapy in transplantation, there has been a significant increase in the incidence of lymphomas (Wilkinson, et al., "Transplantation," 47:293–296, 1989). The chronic failure of immunosuppressive therapy is revealed by the fact that the graft survival rate of 85% at 1 year drops to 67% at 5 years (Kahan, et al., "Am J Kidney Dis," 5:288–295, 1985) in recipients of cadaveric renal transplants receiving triple therapy. Clearly, then the existing immunosuppressive therapy is inadequate. This has stimulated the search for, and development of, new immunosuppressive drugs, and particularly agents that are not directly toxic to either the immune system or to other organ systems. One approach to overcoming the problems associated with present immunosuppressive drugs is the use of biological agents which are actually produced by the animal. An example of such biological agents are the gangliosides.

Gangliosides are a class of glycosphingolipids that have a structure containing a carbohydrate moiety linked to a ceramide. The carbohydrate moiety includes a sugar moiety which has at least one monosaccharide and a sialic acid moiety(s) which includes one or more sialic acid groups (N-acetyl or N-glycolyl neuraminic acid).

Gangliosides are classified according to the number of monosaccharides in the sugar moiety and the number of sialic acid groups present in the sialic acid moiety(s). Further classification is dependent upon where and how many sialic acid(s) are bound to the sugar moiety. For example, the international symbol $G_{M1a}$ designates one of the more common gangliosides which has been extensively studied. The subscript, "M" in the symbol indicates that the ganglioside is a monosialoganglioside and "1" indicates that there are four saccharide units present in the carbohydrate moiety. The subscripts "a", "b" or "c" indicate isomers of the particular ganglioside described which differ in the position of the sialic acid(s). The subscripts "D", "T" and "Q" used in the international ganglioside symbols represent disialogangliosides, trisialogangliosides and tetrasialogangliosides, respectively. The subscripts "2", "3" and "4" represent trisaccharide, disaccharide and monosaccharide gangliosides, respectively. The terminal saccharide is the saccharide which is located at the end of the carbohydrate moiety which is opposite to the end that is attached to the ceramide moiety.

A number of different gangliosides have been identified. These gangliosides are abundant in nerve issue and they are especially abundant in brain tissue. Common gangliosides which have been isolated from brain tissue in significant amounts include $G_{D1a}$, $G_{M1}$, $G_{T1b}$ and $G_{D1b}$. Gangliosides have also been synthetically produced. For example, U.S. Pat. No. 4,918,170 discloses the synthesis of $G_{M3}$ and $G_{M4}$.

It is well known that gangliosides are functionally important in the nervous system and it has been claimed that gangliosides are useful in the therapy of peripheral nervous system disorders. Numerous gangliosides and derivatives thereof have been used to treat a wide variety of nervous system disorders including cerebral ischemic strokes. For example, see U.S. Pat. Nos. 4,940,694; 4,937,232; and 4,716,223. Gangliosides have also been used to affect the activity of phagocytes (U.S. Pat. No. 4,831,021) and to treat gastrointestinal disease-producing organisms (U.S. Pat. No. 4,762,822).

The use of gangliosides and ganglioside analogues to suppress or otherwise affect the immune. system has not yet been investigated as extensively as their use in neurological disorders.

The first report of ganglioside suppression of immune responses in vivo was published twenty years ago by Agarwal and Neter, who discovered inhibition by gangliosides of the primary antibody response to bacterial antigens in mice (Agarwal, et al., *J.Immunol.*, 107:1448–1456, 1971). Recent studies have shown that tumor gangliosides which are shed in vivo enhance tumor formation in mice (Ladisch, et al., *J.Clin.Invest.*, 79:1879–1882, 1987), a finding confirmed by other laboratories (Alessandri, et al., *Cancer Res.*, 47:4243–4347, 1987; Saha, et al., *Int.J.Cancer*, 41:432–435, 1988); indirect evidence (Ladisch, et al., *J.Clin.Invest.*, 79:1879–1882, 1987) suggests that this enhancement occurs by an immunologic mechanism. However, a recent investigation into the in vivo immunosuppressive effect of $G_{M1}$ ganglioside or mixed bovine brain gangliosides (mainly $G_{M1}$, $G_{D1a}$, $G_{D1b}$, and $GT_{1b}$) was conducted by Presti, D. et al., (Presti, D. et al. *J. Neuroimmunology*, 22: 233–239, 1989). The study concluded that there was no evidence of a suppressive effect on humoral or cellular immunity exhibited in vivo by the $G_{M1}$ ganglioside or the mixed brain gangliosides.

Synthetic ganglioside analogues in which the sialic acid moiety has been removed, i.e. desialylated gangliosides (otherwise known as neutral glycophingolipids, NGSL), have been suggested for use to suppress graft rejection in organ transplantation (U.S. Pat. No. 4,388,309).

In view of the above, it would be desirable to establish, in general, whether or not naturally occurring gangliosides can be used effectively as an immune system suppressant. Further, it would also be desirable to establish if any particular type of ganglioside structure or group is exceptionally effective in suppressing the immune system.

SUMMARY OF THE INVENTION

In accordance with the present invention, it was discovered that naturally occurring gangliosides isolated from normal human brain tissue are effective immunosuppressive agents. The gangliosides which were purified from the brain tissue included the major species $G_{M1}$, $G_{D1a}$, $G_{D1b}$, and $G_{T1b}$ and six minor gangliosides $G_{M4}$, $G_{M3}$, $G_{M2}$, $G_{D3}$, $G_{D2}$, and $G_{Q1b}$. These gangliosides were found to have varying degrees of effectiveness as immunosuppressive agents.

As a feature of the present invention, it was discovered that gangliosides having a carbohydrate moiety wherein a sialic acid group is attached to the terminal saccharide group are more effective as an immunosuppressive agent than those gangliosides without a terminal sialic acid group or than the NGSL, which lack sialic acid. In addition, it was discovered that the immunosuppressive activity of gangliosides increases as the number of saccharides in the sugar moiety decreases. Ganglioside $G_{M4}$ was found to be particularly immunosuppressive.

The present invention involves methods and compositions for suppressing an immune response in animals. The method in accordance with the present invention involves administering to the animal an immunosuppressively effective amount of a ganglioside wherein the ganglioside includes a ceramide moiety and a carbohydrate moiety including a sialic acid moiety and a sugar moiety. As a feature of the present invention, the sialic acid moiety includes one or more sialic acid groups which are attached to the terminal monosaccharide of the sugar moiety.

In accordance with the present invention, it was discovered that gangliosides demonstrate a wide range of immunosuppressive activities. Ganglioside $G_{M4}$, which is a monosaccharide ganglioside, was found to have unexpectedly high immunosuppressive activity. Accordingly, a feature of the present invention involves using gangliosides with a low number of saccharide units and having terminal sialic acid groups. Further, the gangliosides are preferably homogeneous with respect to the high activity carbohydrate moiety to enhance the immunosuppressive effect during treatment.

Compositions in accordance with the present invention include physiologically acceptable carriers which contain an immunosuppressive concentration of gangliosides. The compositions are used in accordance with the method of the present invention to treat a wide variety of conditions wherein the immunosuppressive activity of the ganglioside is required. The compositions include gangliosides with terminal sialic acid groups and preferably include gangliosides with a low number of saccharide units. Ganglioside $G_{M4}$. is a preferred ganglioside for use in the compositions of the present invention.

The above-discussed and many other features and attendant advantages of the present invention will become better understood by reference to the following detailed description.

BRIEF DESCRIPTION OF THE DRAWING

The drawing is a schematic representation of the major human brain gangliosides showing their structure and proposed pathways of biosynthesis.

DETAILED DESCRIPTION OF THE INVENTION

The method of the present invention involves treating animals with gangliosides to suppress an immune response.

In accordance with applicant's invention, gangliosides having a terminal sialic acid group are more effective as immunosuppressants than gangliosides with internally located sialic acid groups or desialyl gangliosides (NGSL's). Sialic acid groups are terminal when they are bound to the terminal monosaccharide which is located on the sugar moiety opposite the ceramide moiety. Exemplary gangliosides with terminal sialic acid groups include $G_{M4}$, $G_{M3}$, $G_{M1b}$, $G_{D1a}$, $G_{T1b}$, and $G_{Q1b}$. The terminal sialic acid groups can include up to ten sialic acids. However, gangliosides with sialic acid groups having three or less sialic acids are preferred.

The ten common human brain gangliosides and their biosynthetic pathway are set forth in the FIGURE. The structure of each ganglioside is set forth using conventional abbreviations for the ceramide, saccharide and sialic acid (SA) groups. The FIGURE also outlines the biosynthetic pathway of the gangliosides. The biosynthesis of gangliosides is discussed in detail in S. Roseman, *Chem. Phys. Lipids*, 5: 270–297, 1970.

The gangliosides may be prepared by known isolation procedures from brain or nervous tissue. Alternatively, the gangliosides may be prepared synthetically by procedures such as those set forth in U.S. Pat. No. 4,868,292. The preferred gangliosides are those with sialic acid moieties made up of N-acetyl-neuraminic acid and/or N-glycolylneuraminic acid. Preferred saccharides for the carbohydrate moieties are glucose and galactose. Other suitable saccharides include N-acetyl galactosamine, N-acetylglucosamine and fucose.

It was discovered that the immunosuppressive activity of gangliosides increases as the number of saccharides in the carbohydrate moiety is reduced. Accordingly, it is preferred that gangliosides with a lower number of saccharides be used. Preferably, the ganglioside will be a monosaccharide, such as $G_{M4}$. Another preferred ganglioside is one which does not include a saccharide as part of the carbohydrate moiety, i.e. there is no sugar moiety. The chemical name for this compound would be sialosylceramide. For the purposes of this specification, such gangliosides will be identified as $G_{M5}$. Synthesis of $G_{M5}$ ganglioside is disclosed in the previously mentioned U.S. Pat. No. 4,868,292. It is expected that $G_{M5}$ ganglioside will be as active as $G_{M4}$ with respect to in vivo immunosuppression.

Although the preferred ganglioside structures contain an unsubstituted terminal sialic acid, it will be obvious to those skilled in the art that any ganglioside molecule that can be metabolized in vivo to provide such preferred structures is also within the scope of the present invention. Such gangliosides, for example, include certain ganglioside lactones and similar substituted gangliosides.

As set forth in the examples below, gangliosides bind to plasma proteins and this binding reduces their effectiveness as an immunosuppressant due to competitive inhibition of binding to leukocytes. Accordingly, it is preferred that the gangliosides be introduced into the animal encapsulated in liposomes or packaged in resealed erythrocytes. This protective procedure will be described in detail below. Alternatively, when protection of the ganglioside from plasma protein binding is not possible, the preferred treatment procedure is to increase the dosage to minimize the neutralization effects caused by the plasma proteins.

In the present invention, the term "suppressive" denotes a lessening of the detrimental effect of the undesirable immune response in the animal receiving therapy. The term "immunosuppressively effective" means that the amount of ganglioside used is of sufficient quantity to suppress the cause of disease or symptoms due to the undesirable immune response. The term "animal" also denotes humans.

The dosage ranges for the administration of the gangliosides of the invention are those large enough to produce the desired effect in which the symptoms of the immune response show some degree of suppression. The dosage should not be so large as to cause adverse side effects. Generally, the dosage will vary with the age, condition, sex and extent of the disease in the animal and can be determined by one of skill in the art. The dosage can be adjusted by the individual physician in the event of any counterindications. Dosage can vary from less than 1 mg/kg/dose to about 100 mg/kg/dose, referably about 5 mg/kg/dose to 10 mg/kg/dose, in one or more dose administrations daily.

The gangliosides of the invention can be administered parenterally by single injections or by gradual infusion over time. The gangliosides can be administered intravenously, intraperitoneally, intramuscularly, subcutaneously, intracavitarily, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils, intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Additional pharmaceutical methods may be employed to control the duration of action. Controlled release preparations may be achieved by the use of polymers to complex or adsorb the ganglioside. The controlled delivery may be exercised by selecting appropriate macromolecules (for example, polyesters, polyamino carboxymethylcellulose, and protamine sulfate) and the concentration of macromolecules as well as the methods of incorporation in order to control release. Another possible method to control the duration of action by controlled release preparations is to incorporate the ganglioside into particles of a polymeric material such as polyesters, polyamino acids, hydrogels, poly (lactic acid) or ethylene vinylacetate copolymers.

In order to protect the gangliosides from binding with plasma proteins, it is preferred that the gangliosides be entrapped in microcapsules prepared, for example, by coacervation techniques or by interfacial polymerization, for example, hydroxymethylcellulose or gelatin-microcapsules and poly (methymethacrylate) microcapsules, respectively, or in colloidal drug delivery systems, for example, liposomes, albumin microspheres, microemulsions, nanoparticles, and nanocapsules or in macroemulsions. Such teachings are disclosed in *Remington's Pharmaceutical Sciences* (16th Ed., A. Oslo, ed., Mack, Easton, Pa., 1980).

The gangliosides of the invention are well suited for use in targetable drug delivery systems such as synthetic or natural polymers in the form of macromolecular complexes, nanocapsules, microspheres, or beads, and lipid-based systems including oil-in-water emulsions, micelles, mixed micelles, liposomes, and resealed erythrocytes. These systems are known collectively as colloidal drug delivery systems. Typically, such colloidal particles containing the dispersed gangliosides are about 50 nm–2 µm in diameter. The size of the colloidal particles allows them to be administered intravenously such as by injection, or as an aerosol. Materials used in the preparation of colloidal systems are typically sterilizable via filter sterilization, nontoxic, and biodegradable, for example albumin, ethylcellulose, casein, gelatin, lecithin, phospholipids, and soybean oil. Polymeric colloidal systems are prepared by a process similar to the coacervation of microencapsulation.

Most preferred as a targeted delivery system for the gangliosides of the invention are liposomes. When phospholipids are gently dispersed in aqueous media, they swell, hydrate, and spontaneously form multilamellar concentric bilayer vesicles with layers of aqueous media separating the lipid bilayer. Such systems are usually referred to as multilamellar liposomes or multilamellar vesicles (MLVs) and have diameters ranging from about 100 nm to about 4 $\mu$m. When MLVs are sonicated, small unilamellar vesicles (SUVS) with diameters in the range of from about 20 to about 50 nm are formed, which contain an aqueous solution in the core of the SUV.

The composition of the liposome is usually a combination of phospholipids, particularly high-phase-transition-temperature phospholipids, usually in combination with steroids, especially cholesterol. Other phospholipids or other lipids may also be used.

Examples of lipids useful in liposome production include phosphatidyl compounds, such as phosphatidylglycerol, phosphatidylcholine, phosphatidylserine, and phosphatidylethanolamine. Particularly useful are diacylphosphatidylglycerols, where the lipid moiety contains from 14–18 carbon atoms, particularly from 16–18 carbon atoms, and are saturated. Illustrative phospholipids include egg phosphatidylcholine, dipalmitoylphosphatidylcholine, and distearoylphosphatidylcholine.

In preparing liposomes containing the gangliosides of the invention, such variables as the efficiency of ganglioside encapsulation, lability of the ganglioside, homogeneity and size of the resulting population of liposomes, ganglioside-to-lipid ratio, permeability instability of the preparation, and pharmaceutical acceptability of the formulation should be considered. Szoka, et al, *Annual Review of Biophysics and Bioengineering*, 9:467, 1980; Deamer, et al., in *Liposomes*, Marcel Dekker, New York, 1983, 27: Hope, et al., *Chem. Phys. Lipids*, 40:89, 1986).

The targeting of liposomes has been classified based on anatomical and mechanistic factors. Anatomical classification is based on the level of selectivity, for example, organ-specific, cell-specific, and organelle-specific. Mechanistic targeting can be further distinguished based upon whether it is passive or active. Passive targeting utilizes the natural tendency of liposomes to distribute to cells of the reticulo-endothelial systems (RES) in organs which contain sinusoidal capillaries. Active targeting, on the other hand, involves the alteration of the liposome by coupling the liposome to a specific ligand such as a monoclonal antibody, sugar, glycolipid, or protein, or by changing the composition or size of the liposomes themselves in order to achieve targeting to organs and cell types other than the naturally occurring sites of localization. Alternatively, liposomes may physically localize in capillary beds such as the lung or may be given by site-specific injection.

Another targeted delivery system which can be used with the gangliosides of the invention is resealed erythrocytes. When erythrocytes are suspended in a hypotonic medium, swelling occurs and the cell membrane ruptures. As a consequence, pores are formed with diameters of approximately 200–500 Å which allow equilibration of the intracellular and extracellular environment. If the ionic strength of this surrounding media is then adjusted to isotonic conditions and the cells incubated at 37° C., the pores will close such that the erythrocyte reseals. This technique can be utilized with the gangliosides of the invention to entrap the ganglioside inside the resealed erythrocyte. The resealed erythrocyte containing the ganglioside can then be used for targeted delivery.

The targeted delivery system containing the gangliosides of the invention may be administered in a variety of ways to a host, particularly a mammalian host, such as intravenously, intramuscularly, subcutaneously, intra-peritoneally, intravascularly, topically, intracavitarily, transdermally, intranasally, and by inhalation. The concentration of the gangliosides will vary upon the particular application, the nature of the disease, the frequency of administration, or the like. The targeted delivery system-encapsulated ganglioside may be provided in a formulation comprising other compounds as appropriate and an aqueous physiologically acceptable medium, for example, saline, phosphate buffered saline, or the like.

The above disclosure generally describes the present invention. A further understanding can be obtained by reference to the following specific examples which are provided for purposes of illustration and are not intended to be limiting.

EXAMPLE 1

Preparation and Chemical Characterization of Human Brain Gangliosides and Asialogangliosides Normal human brain tissue was extracted with chloroform-methanol (Ledeen, et al., Methods Enzymol., 83:139–191, 1982) to yield a ganglioside-containing total lipid extract (TLE). The total ganglioside fractions were then purified by partitioning the TLE twice in the solvent mixture of diisopropylether, 1-butanol, and 0.3% aqueous NaCl (6:4:5) (Ladisch, et al., Anal. Biochem., 146:220–231, 1985). Salts and low molecular weight contaminants were removed from the lyophilized final lower aqueous phase by Sephadex G-50 size-exclusion chromatography using double distilled, deionized water as the mobile phase. The gangliosides were recovered in the void volume and lyophilized.

The purified mixture of total human brain gangliosides was separated by normal phase HPLC into individual ganglioside species differing in carbohydrate structure according to the method of Gazzotti, et al., J. Chromatogr., 348:371–378, 1985. 100 nmol portions of total brain ganglioside were chromatographed using the Perkin-Elmer Isopure HPLC system, at ambient temperature on a LiChrosorb-NH$_2$ column (250 mm length, 4 mm i.d., and 7 micron average particle diameter, Merck, Darmstadt, Germany). The elation program consisted of a gradient of the following solvent mixtures; acetonitrile-5 mM Sorensen's phosphate buffer (83:17), pH 5.6, and acetonitrile-20 mM Sorensen's phosphate buffer (1:1) pH 5.6. All solvents used are HPLC grade (Fisher Scientific). The elution profile was monitored by flow-through detection of UV absorbance at 215 nm (Perkin-Elmer LC 90 Bio UV detector). The ganglioside fractions were desalted by Sephadex G-50 size-exclusion chromatography. Nine brain ganglioside species were recovered in this way. They were $G_{M4}$, $G_{M3}$, $G_{M2}$, $G_{M1}$, $G_{D3}$, $G_{D1a}$, $G_{D1b}$, $G_{T1b}$, and $G_{Q1b}$. $G_{D2}$ was prepared by enzymatic (β-galactosidase) removal of the terminal galactose from $G_{D1b}$ and repurified by HPLC. The purified gangliosides were blanketed with nitrogen and stored under anhydrous conditions at −20° C. The homogeneity of the fractions was verified by HPTLC.

Gangliosides were quantitated as nmol lipid-bound sialic acid (LBSA) by the modified calorimetric resorcinol assay (L. Svennerholm, Acta Chem. Scand., 12:547–554, 1958; Miettinen, et al., Acta Chemi.Scand., 13:856–858, 1959). To permit comparison of all data on a molecular basis, the resorcinol assay results are converted to nmol ganglioside by the formula:

$$\text{nmol ganglioside} = \frac{\text{nmol lipid-bound sialic acid measured}}{\text{no. of sialic acids/ganglioside molecule}}$$

In the case of $G_{T1b}$, for example, the divisor is 3.

Initial qualitative characterization of the gangliosides was achieved by high performance thin layer chromatography (HPTLC). 10×20 cm precoated Silica Gel-60 HPTLC plates (Merck, Darmstadt, Germany) which had been activated by desiccation in vacuo over sodium pentoxide were used. The plates were developed in chloroform:methanol:0.25% CaCl$_2$ 2H$_2$O, 60:40:9. Gangliosides were visualized as purple bands with resorcinol-HCL reagent (L.Svennerholm, Biochim.Biophys. Acta, 24:604–611, 1957). Orcinol reagent was used to detect the desialylated (neutral) glycosphingolipids (L. Svennerholm, J.Neurochem., 1:42–53, 1956). The oligosaccharide structure of individual ganglioside molecular species was confirmed by negative-ion fast atom bombardment mass spectroscopy (FABMS) of the intact, underivatized ganglioside molecules (Ladisch, et al., J.Biol.Chem., 264:1209–1215, 1989).

Neutral glycosphingolipids asialo-$G_{M4}$, asialo-$G_{M3}$ asialo-$G_{M2}$, and asialo-$G_{M1}$, were prepared according to the method described by Kasai, et al., (Lipids, 17:107–110, 1982). 30 nmol of each HPLC-purified normal brain ganglioside to be hydrolyzed ($G_{M4}$, $G_{M3}$, $G_{M2}$, and $G_{M1}$) was dissolved in chloroform-methanol 1:1, aliquoted into a 2 ml microvial (Wheaton), and taken to dryness by a stream of $N_2$. 500 µl 0.1N formic acid was then added to each sample. The samples were vortexed, sonicated, heated at 100° C. for 2 hours, cooled to room temperature, neutralized to pH 7 with 0.1N NaOH, and lyophilized. The reaction products were redissolved in 0.3 ml distilled water with sonication. The neutral glycosphingolipids were separated from the free sialic acid liberated by the hydrolysis and the sodium formate by the neutralization reaction, by Sephadex G-50 gel size exclusion chromatography. The asialogangliosides were recovered in the void volume. Completeness of the hydrolysis and purity of the reaction products were confirmed by HPTLC.

EXAMPLE 2

Ganglioside Binding to Peripheral Blood Mononuclear Cells

Aliquots of highly purified total brain gangliosides and HPLC-purified $G_{M2}$ were tritium-labelled as described (G.Schwarzmann, Biochim.Biophys.Acta, 527:106–114, 1978). The gangliosides were oxidized with 1 mM sodium periodate in 0.1 N NaAc, pH 5.5, containing 0.3 M NaCl, at 4° C. After 10 minutes with stirring, the reaction was stopped by the addition of 20 µl glycerol, and the products purified by gel filtration. The product was lyophilized and redissolved in 1.1 ml Sorensen's phosphate buffer #17 (pH 7.4) containing 0.15 M NaCl. 0.4 µCi $NaBH_4$ (50 µl, 0.1M) was added and the solution stirred for 30 minutes at room temperature. Then, 100 µl unlabelled $NaBH_4$ was added and the solution stirred for an additional 30 minutes. Finally, 0.01 M NaAc was added to neutralize the solution. The radiolabelled gangliosides were repurified by Sephadex G-50 gel filtration. Purity of the radiolabelled product (i.e., absence of non-gangliosides associated radiolabel) was confirmed by documenting that the resorcinol-stained and autoradiographic HPTLC patterns of the purified, radiolabelled gangliosides were identical, as described (Wong, et al., J.Lipid Res., 24:666–669, 1983). The specific activity of the total brain gangliosides was $7 \times 10^3$ cpm/nmol, and that of $G_{M2}$ $2.7 \times 10^4$ cpm/nmol.

Gangliosides bind to the proteins and lipoproteins contained in the normal human plasma added to the culture medium. The plasma proteins competitively inhibit gangliosides binding to PBMC. Accordingly, the effect of plasma protein binding on the binding of gangliosides to PBMC was determined as follows.

Ganglioside-PBMC binding was quantitated using the radiolabelled gangliosides prepared above and PBMC. PBMC concentration was adjusted to $5$–$10 \times 10^6$ cells/ml in HB104 containing 0% to 7.5% autologous plasma. The cell suspension was incubated at 37° C. in 15 ml loosely capped polypropylene tubes. $^3$H-gangliosides, mixed brain or HPLC-purified $G_{M2}$, were added to a final concentration of 3–10 µM. Control tubes contained gangliosides in medium alone, without PBMC. Binding of radiolabelled gangliosides to the PBMC was measured as follows: 560 aliquots of the cell suspension were layered over 600 µsilicone oil (Versilube F50 Silicone Fluid, General Electric) in Eppendorf minicentrifuge tubes. Following a 1 minute centrifugation in an Eppendorf Microfuge, the aqueous supernatant was removed completely using a Pasteur pipet, the tube was cut with a razor blade, and the PBMC, which had been pelleted to the bottom of the tube, were recovered. Radioactivity in the supernatant and pellet was quantitated by β scintillation counting, and % binding of radiolabelled gangliosides to the cells calculated. Absolute binding was calculated from knowledge of the specific activity of the gangliosides.

3.1 µM radiolabelled total brain gangliosides were added to PBMC which were incubated in medium containing either 7.5% plasma, or no plasma. 0.1% of the total gangliosides, or $1.8 \times 10^5$ molecules/cell, were bound to the PBMC after a 4 hour incubation in medium containing 7.5% plasma. Binding was dramatically higher (1.6%, or $2.9 \times 10^6$ molecules/cell) when plasma was omitted from the medium.

Similar results were obtained in the investigation of binding of HPLC-purified $G_{M2}$ to PBMC. In the presence of 0.5% plasma, $G_{M2}$-PBMC binding was 2.0% of the ganglioside present in the culture medium, in contrast to only 0.3% binding when the medium contained 7.5% plasma.

EXAMPLE 3

Effect of Plasma Concentration on Inhibition of Lymphoproliferation by Gangliosides The inhibition of the proliferative response of peripheral blood mononuclear cells (PBMC) represents a method by which the immunosuppressive activity of gangliosides can be determined. Inhibition of the proliferative response of PBMC by a given ganglioside or group of gangliosides is measured by determining thymidine uptake of stimulated cells.

Normal human peripheral blood mononuclear cells (PBMC) for use in the lymphocyte proliferation assays were isolated by Ficoll-hypaque density gradient centrifugation (A. Boyum, Scand. J.Clin.Lab.Invest., 21:77–89, 1968) from whole blood collected in preservative-free heparin (50U/ml). The cells were washed three times and resuspended in complete serum-free HB104 medium supplemented with 2 mM L-glutamine, 2 mM sodium pyruvate, 1% HB104 protein supplement (albumin, insulin, and transferring; Hana Biologics), 10 mM HEPES buffer solution to assist in pH control, and autologous human plasma added to a final concentration of 0.5%. As previously shown, this medium allows assays to be conducted in low plasma concentrations without loss of PBMC viability and with preservation of PBMC proliferative responses when the plating is completed expeditiously.

To enhance the usefulness of this method, the total culture volume was reduced by three-fourths over that of a standard assay system by using 96-well half area (A/2) tissue culture clusters (Costar #3696). The problem of evaporation that can occur in these small wells over the course of a 6-day incubation period (particularly in the peripheral wells of the plates) was avoided by using only the center 60 of the 96 wells of each plate and filling the interwell compartments and unused wells with sterile distilled water.

To prepare the cultures (45 µl total volume), first 10 µl ganglioside solution was added/well. Then, the PBMC suspension (25 µl, $2 \times 10^6$ cells/ml complete medium) was added, and PBMC and gangliosides preincubated for 3 hours at 37° C. Finally, 10 µl of the previously determined optimal concentration of the stimulant of lymphoproliferation was added (3.5 Lf/ml basal medium, in the case of tetanus toxoid (Mass. Dept. of Health, Boston, Mass.)). An equal volume of basal medium alone was added to the unstimulated (control) cultures.

The complete cultures were incubated at 37° C. in 95% air/5% $CO_2$. The culture duration is 3 days when the stimulant is a non-specific mitogen (PHA, ConA, PWM) and 6 days to assess antigen-specific responses (tetanus and diphtheria toxoids, candida antigen) (Ladisch, et al., J.Clin.Invest., 74:2074–2081, 1984). At the end of the culture period, 0.5 µCi $^3$H-thymidine in 50 µl medium was added to each well and the cultures incubated for an additional 4.5 hours. The cultures were harvested onto glass fiber filter paper and cellular uptake of $^3$H-thymidine quantitated by β-scintillation counting. Mean net $^3$H-thymidine uptake in stimulated cultures is determined by subtracting the mean cpm of unstimulated cultures. Percent inhibition is calculated by comparing the mean net $^3$H-thymidine uptake of cultures containing gangliosides with that of cultures without gangliosides.

This method was used to further determine the influence of plasma proteins upon immunoregulation by gangliosides, by assessing inhibition of lymphoproliferation using the same plasma and ganglioside concentrations as in Example 2. Whereas significant inhibition (50%) of the lymphoproliferative response of normal PBMC to tetanus toxoid in the presence of 7.5% plasma required a ganglioside concentration of greater than 12.5 µM, the elimination of plasma from the culture medium increased ganglioside activity substantially. Even the lowest ganglioside concentration tested (3.1 µM, 2.9×10$^6$ molecules bound/cell) caused greater than 60% inhibition of lymphoproliferation. These results together with the binding data demonstrate that the mechanism by which high plasma protein concentration counteracts inhibitory effects of the gangliosides upon lymphoproliferation may be by reducing the binding of gangliosides to PBMC and suggest that conditions to enhance binding to PBMC would optimize the immunosuppressive effects of gangliosides administered to animals.

EXAMPLE 4

Immunosuppressive Activity of Gangliosides Against Different Stimulating Antigens To test the generality of inhibition by gangliosides (i.e. to determine whether broad, antigen-independent activity characterizes gangliosides), in two examples, two gangliosides $G_{D1a}$, (a major constituent gangliosides of normal human brain) and $G_{M4}$ the simplest ganglioside structure tested, were assessed for their inhibitory effects against a broad panel of mitogens and antigens using medium containing a low (0.5%) plasma concentration. The results are shown in Table 1.

TABLE 1

INHIBITION OF NORMAL HUMAN LYMPHOPROLIFERATIVE RESPONSES BY HPLC-PURIFIED GANGLIOSIDES $G_{D1a}$ AND $G_{M4}$

| | Ganglioside and Concentration | | | | | |
|---|---|---|---|---|---|---|
| | $G_{D1a}$ | | | $G_{M4}$ | | |
| Stimulant | 0 | 2.5 | 10 | 0 | 2.5 | 10 |
| Non-Specific Mitogens | | | | | | |
| PHA | 77.4[a] | 75.4(3)[b] | 69.2(11) | 70.8 | 67.4(5) | 0.5(99) |
| ConA | 77.9 | 84.3(0) | 49.0(37) | 61.0 | 59.0(3) | 0.3(99)' |
| PWM | 14.0 | 13.0(7) | 4.5(68) | 6.2 | 4.4(29) | 0.1(98) |

TABLE 1-continued

INHIBITION OF NORMAL HUMAN LYMPHOPROLIFERATIVE RESPONSES BY HPLC-PURIFIED GANGLIOSIDES $G_{D1a}$ AND $G_{M4}$

| | Ganglioside and Concentration | | | | | |
|---|---|---|---|---|---|---|
| | $G_{D1a}$ | | | $G_{M4}$ | | |
| Stimulant | 0 | 2.5 | 10 | 0 | 2.5 | 10 |
| Soluble Antigens | | | | | | |
| Diptheria Toxoid | 5.2 | 2.1(60) | 0.8(85) | 45.6 | 7.4(84) | 0.1(>99) |
| Candida Antigen | 5.8 | 3.2(45) | 0.9(84) | 50.4 | 10.4(79) | 0.1(>99) |
| Tetanus Toxoid | 27.1 | 8.8(68) | 3.2(88) | 54.5 | 10.6(81) | 0.1(>99) |

[a] $^3$H-thymidine uptake, net cpm, mean of triplicate cultures; the SEM was consistently <10%.
[b] ( ) = % inhibition Table 1 shows that intact normal human lymphoproliferative responses to all six non-specific mitogens (6–84×10$^3$ net cpm $^3$H-thymidine uptake) and soluble specific antigens (5–55×10$^3$ net cpm) were observed using the medium containing 0.5% plasma (and a total culture volume of only 45 µl). The individual gangliosides tested selectively inhibited the antigen-specific lymphoproliferative responses; for example, at 2.5 µM each ganglioside inhibited each antigen-specific response to a greater degree than it inhibited any of the mitogen-induced responses (TABLE 1). This selective effect is therefore not dependent on which HPLC-purified ganglioside was used to inhibit, or which mitogen or antigen was used to stimulate, the proliferative response of PBMC. Thus, a property of these HPLC-purified gangliosides, and probably of gangliosides in general as a class of immunoregulatory molecules, is that they are selective inhibitors of all soluble specific antigen-induced lymphoproliferative responses, a conclusion that is in agreement with previous findings (Ladisch, et al., Cancer Res., 43:3803–3813; Ladisch, et al., J.Clin.Invest., 74:2074–2081, 1984; Gonwa, et al., Cancer Res., 44:3467–3470, 1984). The degree of inhibition induced by very low ganglioside concentrations was found to be high. For example, only 10 µM $G_{D1a}$ and $G_{M4}$ caused 88% and greater than 99% inhibition of the PBMC proliferative responses to tetanus toxoid. Unexpectedly, the ganglioside $G_{M4}$ had immunosuppressive activity even greater than did the more complex ganglioside $G_{D1a}$. This finding was surprising since the accepted dogma teaches that immunosuppressive activity generally increases with molecular complexity and specifically the number of sialic acid groups.

EXAMPLE 5

Comparison of Immunosuppressive Activity of Individual Gangliosides

The gangliosides and neutral glycosphingolipid samples prepared in Example 1 were dissolved in chloroform:methanol 1:1, aliquoted into sterile 4ml glass vials, and taken to dryness with a stream of $N_2$. Trace residual solvents were removed by an oil pump vacuum. Next, basal (protein-free) HB104 medium (Hana Biologics) was added to the vials. The gangliosides were blanketed with nitrogen, resuspended with mild sonication (2 minutes in a Branson bath sonicator), and added to the culture wells in final concentrations ranging from 0.15 to 20 µM, or 7.5 pmol to 1 nmol per culture.

Each of the gangliosides was assessed for its ability to inhibit tetanus toxoid-induced normal human lymphoproliferation. The combined results (2–3 separate experiments/ganglioside) span a 100-fold ganglioside concentration range of 20 μM to as low as 0.15 μM, or 7.5 pmol/culture. A summary of the results of the tests is set forth in Table 2 expressed as the ganglioside concentration required to cause 90% inhibition of the lymphoproliferative response ($ID_{90}$).

TABLE 2

COMPARISON OF INHIBITORY ACTIVITY OF GANGLIOSIDES WITH DIFFERING CARBOHYDRATE STRUCTURE

| Ganglioside | $ID_{90}$ |
|---|---|
| Monosialo | |
| $G_{M4}$ | 1.5 |
| $G_{M3}$ | 1.6 |
| $G_{M2}$ | 4.3 |
| $G_{M1}$ | 10.7 |
| Disialo | |
| $G_{D3}$ | 4.3 |
| $G_{D2}$ | 5.5 |
| $G_{D1a}$ | 2.3 |
| $G_{D1b}$ | 4.5 |
| Trisialo | |
| $G_{T1b}$ | 2.8 |
| Polysialo | |
| $G_{Q1b}$ | 1.9 |

As is apparent from Table 2, the immunosuppressive activity of the gangliosides increases with decreasing size of the carbohydrate moiety. $G_{M4}$ was found to be the most immunosuppressive ganglioside. This indicates that ganglioside $G_{M5}$ in which the carbohydrate moiety does not contain a saccharide unit will also be very active as an immunosuppressant. Accordingly, the use of such gangliosides in accordance with the present invention is preferred.

The location of the sialic acid groups is also shown in Table 2 to be important in establishing immunosuppressive activity. The gangliosides with terminal sialic acid groups were found to be more immunosuppressive than corresponding gangliosides not having a terminal sialic acid. For example, it was found that $G_{M1b}$ (not shown in Table 2), which has a terminal sialic acid, was very active in contrast to $G_{M1a}$ which was the least active of the gangliosides shown in Table 2.

To further demonstrate the importance of sialic acid in conferring immunosuppressive activity, comparisons were made of the inhibitory activities within a series of homologous gangliosides in which the neutral oligosaccharide portion of the ganglioside molecule is identical in size and sequence, while the number of sialic acids is varied. One such series, $G_{M1}$, $G_{D1b}$, $G_{T1b}$, and $G_{Q1b}$ which all contain the tetrasaccharide backbone Galβ1-3GalNAcβ1-4Glcβ1-1Cer shows a direct influence of the number of sialic acids. Specifically, increasing immunosuppressive activity accompanies increasing number of sialic acids in this homologous series of molecules (TABLE 2). However, this is not an invariable finding. For example, it is not true for two homologous pairs with di- or tri-saccharide backbones, $G_{D3}/G_{M3}$ or $G_{D2}/G_{M2}$, respectively. Rather, this quantitative effect of the number of sialic acids on immunosuppressive activity of a gangliosides seems to be most pronounced when the oligosaccharide chain is most complex. Conversely, when the sugar moiety is most simple, a single terminal sialic acid has the highest activity.

The immunosuppressive activity of the four asialogangliosides described in Example 1 were compared to that of their parent glycosphingolipids, which differ only by the presence of one sialic acid. The absence of this sialic acid resulted in marked reduction or abrogation of immunosuppressive activity. The change was most striking in the case of $G_{M4}$ (which was also the most active ganglioside) and its neutral counterpart, asialo-$G_{M4}$ (galactosylceramide); the removal of sialic acid from $G_{M4}$ caused a more than 60-fold change in the $ID_{50}$ (from 0.2 μm to 13 μm). It is least evident in the case of $G_{M1}$ (the least active of the four monosialogangliosides studied), where removal of sialic acid to form asialo-$G_{M1}$, does not substantially alter activity.

EXAMPLE 6

Inhibition of the Allogeneic (Mixed Leukocyte) Response by Gangliosides

The immunologic response to which graft rejection is closely linked is the mixed leukocyte response (MLC). Therefore, an effective immunosuppressive agent must be able to inhibit this reaction. To demonstrate this immunosuppressive effect for gangliosides in accordance with the present invention, lymphoproliferation assays were performed where allogeneic (unrelated donor) leukocytes were used instead of using a soluble antigen (e.g. tetanus toxoid) to stimulate the T-cell response as in the previous examples. The results of the assays are shown in Table 3. The results show that the ganglioside $G_{M4}$ is a more potent inhibitor of the MLC than the other gangliosides tested.

TABLE 3

Inhibition of the Mixed Leukocyte Response (MLR) by Gangliosides

| Concentration | Ganglioside Tested | | |
|---|---|---|---|
| (μM) | $G_{M4}$ | $G_{M2}$ | $G_{D2}$ |
| 0 (control) | 51* | 51 | 51 |
| 2.5 | 5.6 (88) | 29 (43) | 28 (45) |
| 5 | 0.5 (99) | 8.3 (86) | 14 (73) |
| 10 | 0.2 (>99) | 0.8 (98) | 3.7 (93) |

*$^3$H-thymidine incorporation, mean net cpm × $10^{-3}$
( ) = % inhibition of control response

EXAMPLE 7

Inhibition of Lymphoproliferative Responses by Gangliosides Without Direct Toxic Effects An actual increase in cell number during a culture period is a measure of the generation phase of the T cell response. Also, it can be determined whether a molecule is toxic by establishing if there is a decrease in the number of cells at the end of the culture period, compared to controls. $G_{M4}$ was tested for its effect on T cell response and toxicity as follows.

The viable cell counts of unstimulated PBMC incubated in the presence or absence of 5 μM of $G_{M4}$, and measured at the end of the culture period were found to be equal (5.4 and 5.6×$10^5$/ml), for a cell recovery of 54 and 56% of the initial 1.0×$10^6$/ml. This shows that there is no increased cell loss or direct cytotoxicity attributable to the presence of the $G_{M4}$ ganglioside. Tetanus toxoid stimulation caused a 215% increase in cell number from the initial concentration (to 2.15×$10^6$ cells/ml). This demonstrated the expected T cell proliferative response of cultures incubated in the absence of a ganglioside, such as $G_{M4}$. However, in the presence of 5

µM $G_{M4}$, the response to tetanus toxoid was completely ablated; the cell count was $5.1 \times 10^5$/ml, or equivalent to the unstimulated control or ganglioside-treated cultures above. These results confirm that the exposure to $G_{M4}$ caused complete failure of the T cell proliferative response without any reduction in baseline viability.

The contents of the patents, literature articles, and other references referred to in this specification are hereby incorporated by reference.

Those skilled in the art will recognize, or be able to ascertain using no more than routine experimentation, many equivalents to the specific embodiments of the invention specifically described herein. Such equivalents are intended to be encompassed within the spirit and scope of the following claims.

What is claimed is:

1. A method for suppressing an immune response in an animal which comprises administering to the animal an immunosuppressively effective amount of a ganglioside wherein said ganglioside is $G_{M4}$.

2. A method of suppressing an immune response according to claim 1 wherein said ganglioside is administered together with a pharmacologically inert carrier.

3. A method of suppressing an immune response according to claim 1 wherein said ganglioside is encapsulated in a liposome prior to administration to said animal.

4. A method of suppressing an immune response according to claim 1 wherein said ganglioside is packaged in a resealed erythrocyte prior to administration to said animal.

5. A composition for suppressing an immune response in an animal upon administration to said animal, said composition consisting essentially of:

an immunosuppressive concentration of a ganglioside, wherein said ganglioside is $G_{M4}$; and a physiologically acceptable carrier for said ganglioside.

6. A composition for suppressing an immune response according to claim 5 wherein said ganglioside is encapsulated in liposomes.

7. A composition for suppressing an immune response according to claim 5 wherein said ganglioside is packaged in resealed erythrocytes.

* * * * *